United States Patent [19] [11] Patent Number: 4,980,372
Nakai et al. [45] Date of Patent: Dec. 25, 1990

[54] BENZOYLAMINOPHENOXYBUTANOIC ACID DERIVATIVES

[75] Inventors: Hisao Nakai; Hiroshi Terashima, both of Takatsuki; Yoshinobu Arai, Osaka, all of Japan

[73] Assignee: Ono Pharmaceutical Co., Ltd., Osaka, Japan

[21] Appl. No.: 191,193

[22] Filed: May 6, 1988

[30] Foreign Application Priority Data

May 11, 1987 [JP] Japan ................................. 62-112618
Sep. 17, 1987 [JP] Japan ................................. 62-231194

[51] Int. Cl.$^5$ ..................... C07C 321/00; A61K 31/21
[52] U.S. Cl. ..................................... 514/510; 514/538; 514/542; 514/563; 560/9; 560/10; 560/12; 560/13; 560/17; 560/45; 562/427; 562/428; 562/426; 562/430; 562/431; 562/455
[58] Field of Search .................. 560/9, 10, 12, 17, 45, 560/13; 562/427, 430, 431, 455, 426, 428; 514/510, 538, 542, 563

[56] References Cited

U.S. PATENT DOCUMENTS 3,549,689 12/1970 Frey ..................................... 260/471
4,780,469 10/1988 Toda ..................................... 514/456

FOREIGN PATENT DOCUMENTS 181568 5/1986 European Pat. Off. .
1077936 8/1967 United Kingdom .
1088295 10/1967 United Kingdom .

Primary Examiner—Michael L. Shippen
Attorney, Agent, or Firm—Stevens, Davis, Miller & Mosher

[57] ABSTRACT

A benzoylaminophenoxybutanoic acid derivative of general formula:

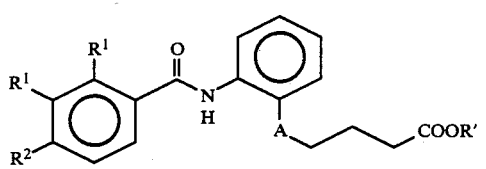

(I)

[wherein $R^1$ represents hydrogen atom or alkyl group of from 1 to 4 carbon atoms(s),
A represents oxygen atom, sulfur atom or sulfinyl (SO) group, two $R^1$s represents methyl groups or chlorine atoms at the same time or cyclopentane, cyclohexane or benzene ring together with the carbon atoms of benzene ring each attaching,
$R^2$ represents a group of general formula:

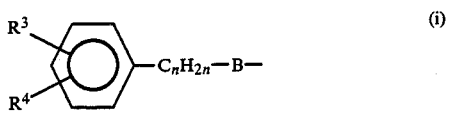

(i)

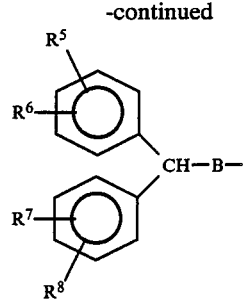

(ii)

or

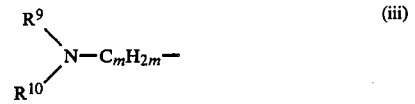 (iii)

{wherein B represents oxygen atom, sulfur atom or a group of general formula:
$NR^{11}$(wherein $R^{11}$ represents hydrogen atom or alkyl group of from 1 to 4 carbon atom(s)),
$R^3$, $R^4$, $R^5$, $R^6$, $R^7$ and $R^8$ represent, independently, hydrogen atom, alkyl group of from 1 to 4 carbon atom(s) halogen atom, trifluoromethyl group or cyclobutylmethyl group,
m represents 0 or 1,
n represents an integer of from 1 to 5, and
$R^9$ and $R^{10}$ represent, independently, hydrogen atom, alkyl group of from 1 to 5 carbon atom(s) or a group of general formula:

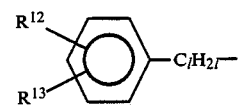

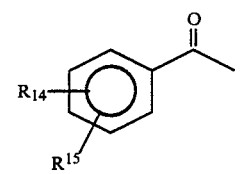

or

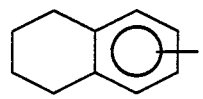

(wherein $R^{12}$, $R^{13}$, $R^{14}$ and $R^{15}$ represent, independently, hydrogen atom, alkyl group of from 1 to 4 carbon atom(s), halogen atom, trifluoromethyl group or cyclobutylmethyl group, and
l represents an integer of from 1 to 4). With the proviso that $R^9$ and $R^{10}$ do not represent hydrogen atoms at the same time}]

and non-toxic salts thereof possess an inhibitory activity on 5α-reductase, and therefore be useful for treating and/or preventing agent for alopecia, acnes or prostatic hypertrophy. 11 Claims, No Drawings

BENZOYLAMINOPHENOXYBUTANOIC ACID DERIVATIVES

SUMMARY

This invention is related to novel compounds having an inhibitory activity on 5α-reductase of the following general formula:

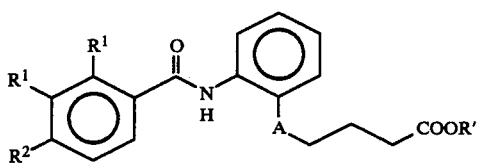

[wherein all of the symbols are the same meaning as hereafter defined.]

BACKGROUND

So far as the origin of androgenic alopecia, many theories are exposited such as (1) imbalance of hormones, (2) genetics, (3) circulatory failure, (4) nutrition.

And it has been also suggested that testosterone (androgenic hormone) played an important role on the generation of hairs.

The theory of Adachi et al which proved the relation between testosterone and androgenic alopecia by biochemical experiments is as follows:

(i) first, testosterone biosynthesized in testis is converted into dihydrotestosterone by 5α-reductase existed in hair follicle, sebaceous gland etc. at the head.

(ii) dihydrotestosterone reduces the activities of adenyl cyclase remarkably.

(iii) it induces fall of the level of cyclic-AMP in cells.

(iv) last, it induces lowering of energy generation of hairs and the limbus and supressing of protein synthesis (See Biochem. Biophys. Res. Commun., 41, 884 (1970)).

According to the theory it is thought that the results of the series of phenomena, hairs in the growing phase shift to the resting phase, the terminal hairs change to the soft hairs, and the androgenic alopecia develops in the end.

A report by H. V. Schweikert supports this theory that large quantities of metabolites by 5α-reductase such as dihydrotestosterone etc. in hair follicles of androgenic alopecia-patent exist more than that in females or healthy males. (See J. Clin. Endocr., 38, 811 (1974)).

It was reported that dihydrotestosterone converted from testosterone by 5α-reductase also plays an important physiological role in the generation of acnes (acne, pimple etc.) other than androgenic alopecia. J. B. Hay et al reported that the metabolism of testosterone by 5α-reductase was enhanced in the affected part of the skin and the acne aggravated, from the study in the flux between affected skin of acne-patient and healthy skin (See Br. J. Dermatol., 91, 123 (1974)).

G. Sansone et al found that synthetic ability of dihydrotestosterone from testosterone developed from two to twenty times in the affected part of acne-patient compared to that in healthy man, and they suggested that dihydrotestosterone generated by 5α-reductase greatly relates to the generation or aggravation of acne (See J. Invest. Dermatol., 56, 366 (1971)).

And, dihydrotestosterone is related to the hypertrophy of prostate. Cowan et al reported that large amount of dihydrotestosterone existed in the prostate of prostatic hypertrophy-patient (See J. Steroid Biochemistry, 11, 609 (1979)). Recently, it was known that activity of 5α-reductase in prostate of prostatic hypertrophy-patient aggravated abnormally (See J. Clinical Endocrinol and Metabolism, 56, 139 (1983)).

From this information it has been clear that dihydrotestosterone also plays an important role in the generation and the development of prostatic hypertrophy.

Prior arts and comparison with them

From the above background, recently, researches and developments of 5α-reductase inhibitors are carried out energetically and they are mainly steroids or derivatives thereof.

Widespread investigation has been carried out in order to discover compound which have a non-steroidal structure, and possess inhibitory activity on 5α-reductase. The present applicants have found that the above purpose can be accomplished by compounds wherein cinnamic acid or benzoic acids form amide bonds with anilines, and then applied for the patents [See ① Japanese Patent Kokai No. 60-97946, ② Japanese Patent Kokai No. 60-116657, ③ Japanese Patent Kokai No. 60-142936, ④ Japanese Patent Kokai No. 60-142941, ⑤ Japanese Patent Kokai No. 60-146855, ⑥ Japanese Patent Kokai No. 61-126061, ⑦ Japanese Patent Kokai No. 62-198652 and 8 Japanese Patent Kokai No. 62-198653.]

For example, in the application ⑥, it was disclosed that a series of compounds of general formula (extracted partially):

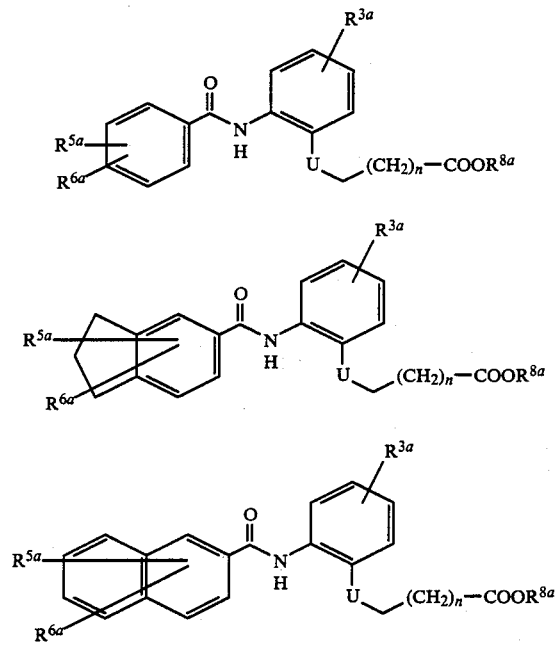

[wherein, $R^{3a}$ represents hydrogen atom, halogen atom etc., $R^{5a}$, $R^{6a}$ represent independently, hydrogen atom, or halogen atom, or straight or branched chain alkyl, alkenyl or alkynyl group of from 1 to 20 carbon atom(s) which may be replaced optional one, two, three, four or five carbon atom(s) by oxygen atom, sulfur atom, halogen atom, nitrogen atom, benzene ring, thiophene ring, naphthalene ring, carbocyclic ring of from 4 to 7 carbon atoms, carbonyl group, carbonyloxy group, hydroxy group, carboxy group, azido group, nitro group, $R^{8a}$ represents hydrogen atom or straight or branched chain alkyl group of from 1 to 6 carbon atom(s), U represents oxygen atom or sulfur atom, and n represents an integer of from 1 to 10.] possess inhibitory activity on 5α-reductase, antagonistic activity on SRS, inhibitory activity on aldose reductase and inhibitory activity on phospholipase.

In the general formula of the application ⑥, if $R^{5a}$ (or $R^{6a}$) group takes phenylalkoxy group which may be substituted, the group will correspond to the $R^2$ group in the compounds of the present invention. In this case, $R^{6a}$ (or $R^{5a}$) rests, as one substituent.

Substituent(s) corresponding to the above substituent are two $R^1$s, but the feature of the compounds of the present invention is:

I these substituents invariably exist at the ortho and meta positions, and

II the number of the substituents is two.

On these points, compounds of the present invention are different from that of the application ⑥ in structure.

In other words, it is an essential condition that two $R^1$s represents the substituents defined above.

Further, several compounds similar to the compounds of the present invention in structure are; e.g. ⑨ British Patent No. 1077936, ⑩ British Patent No. 1088295, ⑪ U.S. Pat. No. 3,549,689, ⑫ PCT Patent Publication No. 8605779.

But the purpose of these applications are invention of compounds having anti-inflammation (including antagonistic activity of SRS), and are different from the purpose of the present invention i.e. to invent compounds having inhibitory activity on 5α-reductase. In their constitution, the compounds of these applications are different from the compounds of the present invention structurally.

Compounds disclosed in the applications ⑨, ⑩ and ⑪ are shown in the following general formula (each of them are extracting partially):

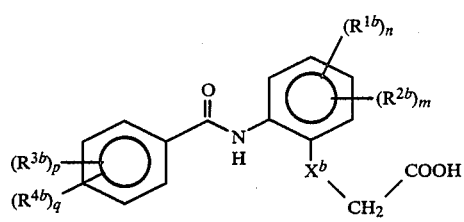

(wherein, $R^{1b}$–$R^{4b}$ each represent alkyl or alkoxy group of from 1 to 4 carbon atom(s), hydroxy group, halogen atom, perhaloalkyl group of from 1 to 4 carbon atom(s), nitro group, alkylsulfonyl group of from 1 to 4 carbon atom(s), $X^b$ represents, oxygen atom or sulfur atom, and m, n, p, q each represent zero or one.)

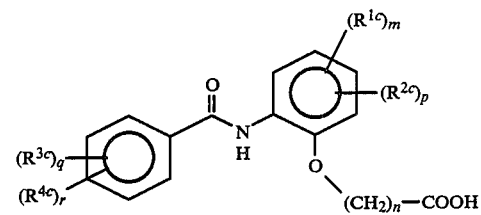

(wherein, $R^{1c}$–$R^{4c}$ each represent alkyl or alkoxy group of from 1 to 4 carbon atom(s), trifluoromethyl group or halogen atom, n represents 2 or 3, m, n, p, q each represents 0 or 1.)

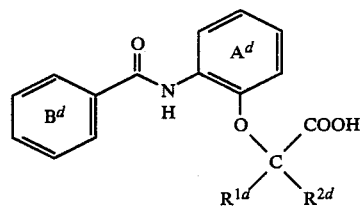

(wherein, $R^{1d}$ represents hydrogen atom or methyl group, $R^{2d}$ represents methyl or ethyl group, $A^d$ ring may be substituted methyl, halogen atom etc., and $B^d$ ring may be substituted by one or two of nitro group, trifluoromethyl group, chlorine atom, fluorine atom or alkyl or alkoxy group of from 1 to 4 carbon atom(s).)

At the substituents $R^{3b\sim c}$ and $R^{4b\sim c}$, and at the substituent(s) on the $B^d$ ring, compounds shown in ⑨ and ⑩, and compounds shown in ⑪ are different from the compounds of the present invention, respectively. The substituted moiety of the compounds of the present invention corresponding are (substituted) phenylalkoxy group.

Patent publication 12 discloses compounds shown in the following general formula (partial extraction):

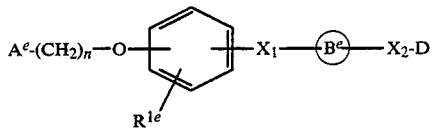

[wherein, $A^e$ represents hydrogen atom, phenyl or phenoxy group, n represents 3~10, $R^{1e}$ represents hydrogen atom or lower alkoxy group, $X^1$ represents —CONH— etc., $B^e$ represents

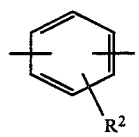

etc. (wherein, $R^2$ represents hydrogen atom, halogen atom, nitro group etc.) $X^2$ represents —O—$Y^4$— etc. (wherein $Y^4$ represents alkylene group of from 1 to 6 carbon atom(s) etc.), and D represents carboxy group, alkoxycarbonyl group etc.].

$R^{1e}$ group in the above formula of the patent publication ⑫ corresponds to two $R^1$ group in the general formula (I) of the present invention. But, they have distinct structures each other (substituent(s), number of the substituent(s), position of the substituent(s)), in i.e., $R^{1e}$ group in the compounds of patent publication represents hydrogen atom or alkoxy group, and two $R^1$s in the compounds of the present invention do represent dimethyl, dichloro, cyclic ring or benzene ring.

Described before, it is an essential condition that two $R^1$s represent the substituents defined above.

DISCLOSURE OF THE INVENTION

The present invention is related to
(1) A benzoylaminophenoxybutanoic acid derivative of general formula:

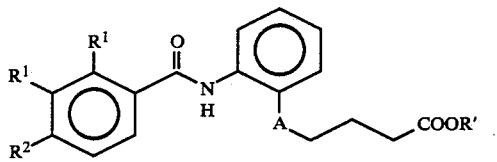
(I)

[wherein R' represents hydrogen atom or alkyl group of from 1 to 4 carbon atom(s), A represents oxygen atom, sulfur atom or sulfinyl (SO) group, two $R^1$s represent methyl groups or chlorine atoms at the same time or cyclopentane, cyclohexane or benzene ring when taken together with the carbon atoms of the benzene ring to which they are attached, $R^2$ represents a group of general formula:

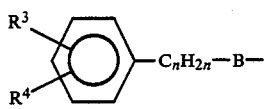
(i)

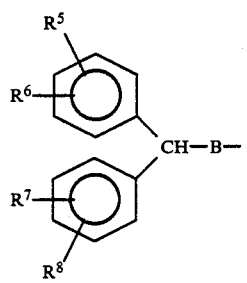
(ii)

or

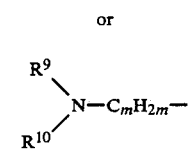
(iii)

{wherein B represents oxygen atom, sulfur atom or a group of general formula: $NR^{11}$ (wherein $R^{11}$ represents hydrogen atom or alkyl group of from 1 to 4 carbon atom(s)), $R^3$, $R^4$, $R^5$, $R^6$, $R^7$ and $R^8$ represent, independently, hydrogen atom, alkyl group of from 1 to 4 carbon atom(s), halogen atom, trifluoromethyl group or cyclobutylmethyl group, m represents 0 or 1, n represents an integer of from 1 to 5, and $R^9$ and $R^{10}$ represent, independently, hydrogen atom, alkyl group of from 1 to 5 carbon atom(s) or a group of general formula:

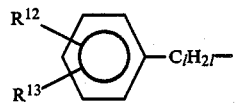

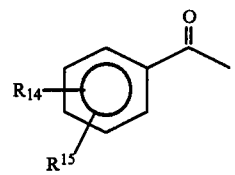

or

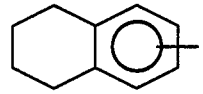

(wherein $R^{12}$, $R^{13}$, $R^{14}$ and $R^{15}$ represent, independently, hydrogen atom, alkyl group of from 1 to 4 carbon atom(s), halogen atom, trifluoromethyl group or cyclobutylmethyl group, and l represents an integer of from 1 to 4.). With the proviso that $R^9$ and $R^{10}$ do not represent hydrogen atoms at the same time; and non-toxic salts thereof.

(2) Process for the preparation of them and (3) Inhibitory agent on 5α-reductase containing them as active ingredient.

Throughout the present application, all of the isomers are included unless specifically excluded. For example, alkyl or alkylene group includes straight and branched ones, and the present invention includes isomers generated by the existence of asymmetric carbon atom e.g. the existence of branched alkyl group.

In the general formula (I), alkyl group of from 1 to 4 carbon atom(s) represented by R', $R^3$-$R^8$, and $R^{11}$-$R^{15}$ means methyl, ethyl, propyl and butyl groups and isomeric groups thereof.

In the general formula (I), alkyl group of from 1 to 5 carbon atom(s) represented by $R^9$ and $R^{10}$ means alkyl groups described above including pentyl group and isomeric groups.

In the general formula (I), halogen atom represented by $R^3$-$R^8$ and $R^{11}$-$R^{15}$ means fluorine, chlorine, bromine and iodine atoms.

In $R^2$ of the general formula (I), general formula —$C_nH_{2n}$— means straight or branched chain alkylene group of from 1 to 4 carbon atom(s). Concretely, it means methylene, ethylene, trimethylene and tetramethylene groups and isomeric groups thereof.

In $R^2$ of the general formula (I), general formula —$C_lH_{2l}$— means straight or branched chain alkylene group of from 1 to 5 carbon atom(s). Concretely, it means alkylene groups described above including pentamethylene group and isomeric groups thereof.

In $R^2$ of the general formula (I), general formula —$C_mH_{2m}$— means single bond or methylene group.

Salts

The compounds of the general formula (I) may be converted into the corresponding salts by known methods. Non-toxic and water-soluble salts are preferable. Suitable salts, for example, are follows: salts of alkaline metal (sodium, potassium etc.), salts of alkaline earth metal (calcium, magnesium etc.), ammonium salts, salts of pharmaceutically acceptable organic amine (tetramethyl)ammonium, triethylamine, methylamine, dimethylamine, cyclopentylamine, benzylamine, phenethylamine, piperidineamine, monoethanolamine, diethanolamine, tris(hydroxymethyl)aminomethane, lysine, arginine, N-methyl-D-glucamine etc.).

Process for the preparation (1)

Among the compounds of the general formula (I), compounds of general formula:

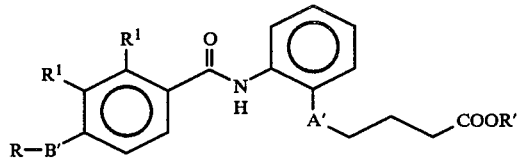

[wherein A' represents oxygen atom or sulfur atom, R represents a group of general formula:

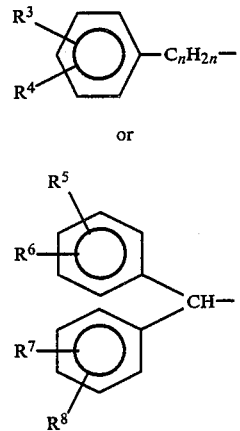

(wherein each symbols are the same meaning as defined hereinbefore.), B' represents oxygen atom or sulfur atom, and the other symbols are the same meaning as defined hereinbefore.] may be prepared by condencing a carboxylic acid of general formula:

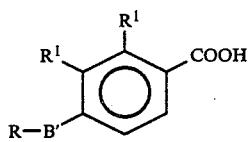

[wherein all of the symbols are the same meaning as defined hereinbefore.] with an amine of general formula:

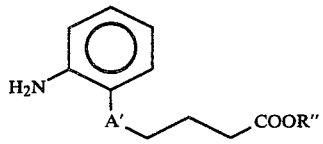

[wherein R" represents alkyl group of from 1 to 4 carbon atom(s) and the other symbols are the same meaning as defined hereinbefore.] and further, if desired, subjecting to hydrolysis the resulting compound.

Reaction to form amide bond with a carboxylic acid and an amine is known, and it may be carried out, for example, by (A) method using mixed acid anhydride,
(B) method using acid halide,
(C) method using condensing agent such as DCC.

Concrete description of these method are follows:

(A) Method using mixed acid anhydride may be carried out, for example, by reacting a carboxylic acid of the general formula (II) and an acid halide (pivaloyl chloride, tosyl chloride, mesyl chloride, etc. or an acid derivative (ethyl chloroformate, isobutyl chloroformate, etc.) in the presence of a tertiary amine (pyridine, triethylamine, picoline etc.) in an inert organic solvent (chloroform, methylene chloride diethyl ether, THF etc.) or without solvent, at a temperature of from 0° C. to 40° C. to give a mixed acid anhydride. And the mixed acid anhydride obtained is reacted with an amine of the general formula (III) in an inert organic solvent (described above), at a temperature of from 0° C. to 40° C.

(B) Method using acid halide may be carried out, for example, by reacting a carboxylic acid of the general formula (II) and the acid halide (thionyl chloride, oxalyl chloride etc.) in the inert organic solvent (described above) or without solvent, at a temperature of from 20° C. to refluxing temperature of the solvent used to give an acid halide. And the acid halide obtained is reacted with an amine of the general formula (III) in the presence or absence of the tertiary amine (described above) in the inert organic solvent (described above), at a temperature of from 0° C. to 40° C.

(C) Method using a condensing agent such as DCC (dicyclohexylcarbodiimide) may be carried out, for example, by reacting a carboxylic acid of the general formula (II) and an amine of the general formula (III), using DCC etc. in the presence or absence of the tertiary amine (described above), in the inert organic solvent (described above) or without solvent, at a temperature of from 0° C. to 40° C.

The reactions of (A), (B) and (C) are carried out, preferably, in an atmosphere of inert gas (argon, nitrogen etc.) and on anhydrous condition.

Conversion of an ester into corresponding acid (saponification) is known, and it may be carried out, for example, using an aq. solution of alkali (lithium hydroxide, potassium hydroxide, sodium hydroxide, potassium carbonate, sodium carbonate etc.) in a water-miscible organic solvent (dimethoxyethane, THF, dioxane, ethanol, methanol, DMSO etc.). The reaction is carried out at a temperature of from −10° C. to 100° C.

Process for the preparation (2)

Among the compounds of the general formula (I), compounds of general formula:

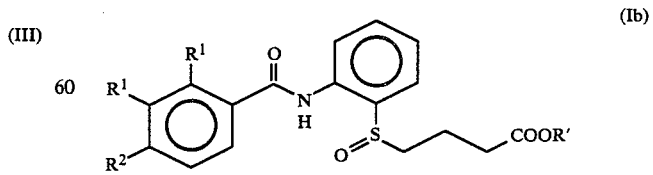

[wherein all of the symbols are the same meaning as defined hereinbefore.] may be prepared by oxidizing a compound, i.e. compounds of the general formula (I) wherein A' is sulfur atom, of general formula:

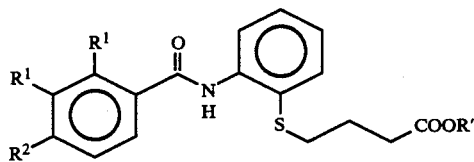 (Ib')

[wherein all of the symbols are the same meaning as defined hereinbefore.]

Oxidation is known, and it may be carried out, for example, using an aq. solution of periodate (sodium periodate etc.), in a water-miscible organic solvent (methanol, ethanol, THF etc.), at a temperature of from 0° C. to 50° C.

Process for the preparation (3)

Among the compounds of the general formula (I), compounds wherein A is oxygen atom or sulfur atom and B is a group of the general formula $NR^{11}$ (wherein $R^{11}$ is the same meaning as defined hereinbefore.) and compounds wherein $R^2$ represents a group of the general formula (iii), i.e. compounds of general formula:

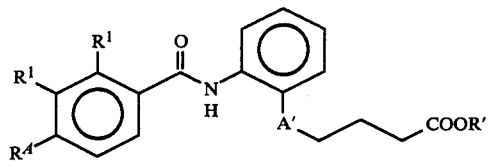 (Ic)

[wherein $R^4$ represents a group of general formula:

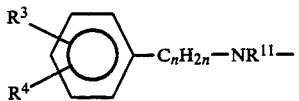 (i')

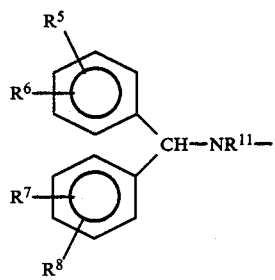 (ii')

or

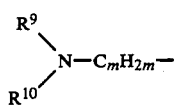 (iii')

(wherein all of the symbols are the same meaning as defined hereinbefore.) and the other symbols are the same meaning as defined hereinbefore.] may be prepared by reacting a compound of general formula:

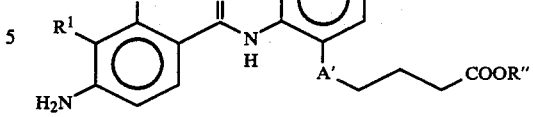 (IV)

[wherein all of the symbols are the same meaning as defined hereinbefore.] and a compound of general formula:

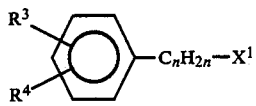 (V)

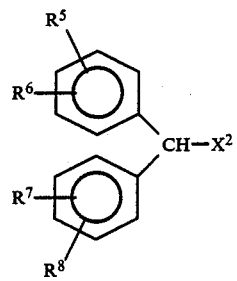 (VI)

$R^9—X^3$ (VII)

$R^{10}—X^4$ (VIII)

and/or $R^{11}—X^5$ (IX)

[wherein $X^1$, $X^2$, $X^3$, $X^4$ and $X^5$ each represent halogen atom, tosyl group or mesyl group.] and further, if desired, subjecting the resulting compound to hydrolysis (saponification; described hereinbefore) or by reacting a compound of general formula:

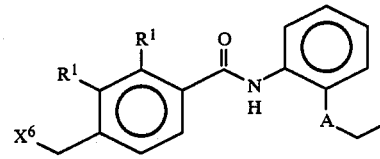 (X)

[wherein $X^6$ represents halogen atom, tosyl group or mesyl group, and the other symbols are the same meaning as defined hereinbefore.] and a compound of general formula:

 (XI)

[wherein all of the symbols are the same meaning as defined hereinbefore.] and further, if desired, subjecting to hydrolysis (saponification; described hereinbefore) of the resulting compound.

These reactions (N-alkylation) are known and they may be carried out, for example, using an aq. or non-aq. solution of alkali (potassium carbonate, sodium hydrocarbonate etc.), in a water miscible organic solvent (methyl ethyl ketone, acetonitrile, propanol, DMF etc.)

Intermediates of the general formula (II), (III), (IV) and (X) may be prepared to follow the reaction scheme (A) described in the next page.

Every reaction in reaction scheme is known and each symbols represent the following meanings or as defined hereinbefore, respectively.

$X^7$—halogen atom, tosyl group or mesyl group,
$R^{20}$—alkyl group of from 1 to 4 carbon atom(s).

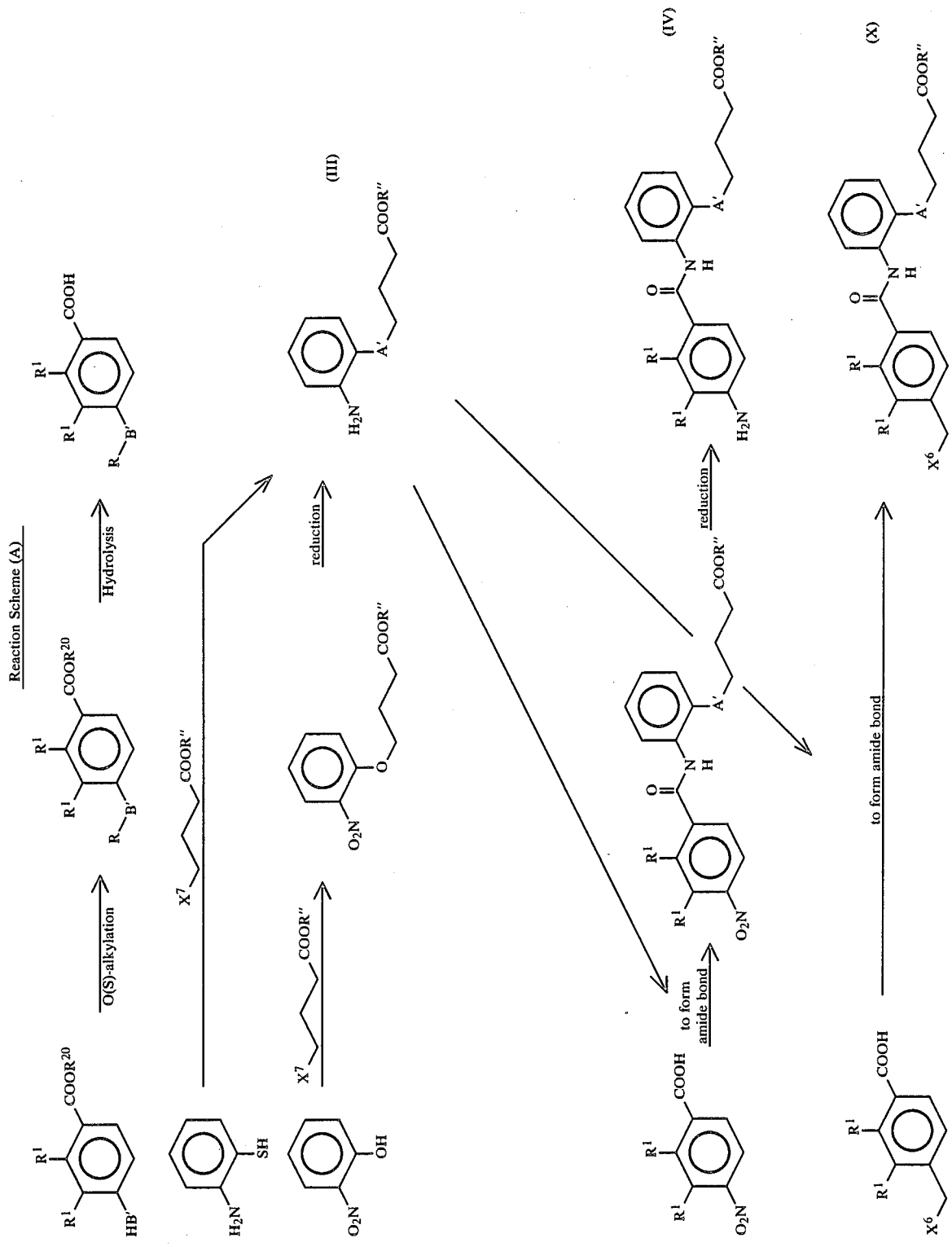

Throughout the specification, in each reactions, products may be purified by conventional methods, for example, distillation at atmospheric or reduced pressure, high performance liquid chromatography, thin layer chromatography using silica gel or magnesium silicate or washing or recrystallization. Purification may be carried out after each reactions or a series of reactions.

Starting Materials

Starting materials and reagents in the present invention are known per se or may be prepared by known methods.

Pharmacological Activities

The compounds of the present invention of the general formula (I) possess an inhibitory activity on 5α-reductase, described before, for example, in a standard laboratory test, results in the followings are given.

5α-reductase inhibitory activity in vitro

The compounds of the present invention showed activities as in the following Table I, with the test system described hereafter.

TABLE I

5α-reductase inhibitory activity

| Example No. of the compound | $IC_{50}$ ($\mu M$) | Example No. of the compound | $IC_{50}$ ($\mu M$) |
|---|---|---|---|
| 2(a) | 2.1 | 2(m) | 0.75 |
| 2(b) | 0.38 | 2(n) | 0.95 |
| 2(c) | 1.3 | 2(o) | 0.005 |
| 2(d) | 0.98 | 2(p) | 0.011 |
| 2(e) | 1.4 | 2(q) | 0.2 |
| 2(f) | 0.27 | 2(x) | 2.8 |
| 2(g) | 0.34 | 2(y) | 0.41 |
| 2(h) | 0.26 | 2(z) | 0.05 |
| 2 | 0.12 | 2(aa) | 0.52 |
| 2(i) | 2.0 | 2(bb) | 0.42 |
| 2(j) | 2.5 | 2(cc) | 0.38 |
| 2(k) | 2.6 | 2(dd) | 0.12 |
| 2(l) | 1.0 | 3 | 0.70 |

Inhibitory activity on 5α-reductase in vitro was measured by the following test system.

The test was carried out by making reference to the method of J. Shimazaki et al [See Endocrinical. Japon., 18, 179 (1971)].

Male rats' prostate (4 g) was homogenized with its triple volume of 0.1M HEPES buffer (pH 7.4) including 0.25M cane sugar, and was centrifuged at 3000 r.p.m. for 10 mins.

The precipitate was suspended into the buffer solution described above (10 ml), and the suspension was centrifuged at 3000 r.p.m. for 5 mins. The resulting precipitated was suspended in the buffer solution (3 ml) described above and was used as a sauce of enzyme.

A reaction mixture (total volume 0.1 ml) of [4-$C^{14}$]-testosterone (1.5 n mol, $1.5 \times 10^5$ cpm) NADPH (0.5 $\mu$mol) enzyme solution (0.03 ml) described above and several kinds of concentration of the compounds in the present invention was incubated for 60 mins at 37° C. Enzyme reaction was quenched by addition of a mixture (1.0 ml) of diethyl ether, petroleum ether and acetic acid (80:20:1), and the mixture was centrifuged at 3000 r.p.m. for 5 mins. The supernatant (200 $\mu$l) was spotted on silica gel thin layer plate. The spot on the plate was developed with a mixture of chloroform, methanol and acetic acid (99:0.8:0.2). Radioactivity of dihydrotestosterone generated on the plate was measured by TLC scanner of radio-autography and inhibitory ratio was calculated.

Toxicity

On the other hand, it was confirmed that the toxicity of the compounds of the present invention were very low. Therefore, the compounds of the present invention may be considered to be sufficiently safe and suitable for pharmaceutical used.

Application for the Pharmaceuticals

To inhibit 5α-reductase is to prevent the excess generation of dihydrotestosterone, described before, and therefore be useful for prevention and/or treatment for alopecia such as male type alopecia, acne and prostatic hypertrophy in animals including human beings, especially human beings.

The compounds of the present invention possess a inhibitory activity on 5α-reductase in vitro, so it is expected to be useful for prevention and/or treatment of alopecia such as male type alopecia, acne and prostatic hypertrophy.

For the purpose above described, the compounds of the present invention may normally by administered systemically (mainly in the case of prevention and/or treatment prostatic hypertrophy) or partially (mainly in the case of prevention and/or treatment of alopecia and acne), usually by oral or parenteral administration.

The doses to be administered are determined depending upon age, body weight, symptom, the desired therapeutic effect, the route of administration, and the duration of the treatment etc. In the human adult, for the treatment and/or prevention of prostatic hypertrophy, the doses per person per dose are generally between 1 mg and 1 g, by oral administration, up to several times per day, and between 100 $\mu$g and 100 mg, by parenteral administration (preferably intravenous administration) up to several times per day.

In the human adult, for the treatment and/or prevention of alopecia and/or acne, the doses per person per dose are generally between 10 $\mu$g and 50 mg, by dermal administration up to several times per day.

As mentioned above, the doses to be used depend upon various conditions. Therefor, there are cases in which doses lower than or greater than the ranges specified above may be used.

In the administration, the compounds of the present invention was administered as solid compositions, liquid compositions and other compositions for oral administration and injections, external compositions and suppositories etc. for parenteral administration.

Solid compositions for oral administration, include compressed tablets, pills, dispersible powders, capsules, and granules. In such compositions, one or more of the active compound(s) is or are, admixed with at least done inert diluent (lactose, mannitol, glucose, hydroxypropylcellulose, microcrystalline cellulose, starch, polyvinylpyrrolidone, magnesium metasilicate alminate etc.). The compositions may also comprise, as is normal practice, additional substances other than inert diluents: e.g. lubricating agents (magnesium stearate etc.), disintegrating agents (cellulose calcium gluconate etc.), and assisting agent for dissolving (glutamic acid, aspertic acid etc.) stabilizing agent (lactose etc.).

The tablets or pills may, if desired, be coated with gastric or enteric material (sugar, gelatin, hydroxypropylcellulose or hydroxypropylmethyl cellulose phthalate etc.).

Capsules include soft ones and hard ones.

Liquid compositions for oral administration include pharmaceutically-acceptable emulsions, solutions, suspensions, syrups and elixirs.

In such compositions, one or more of the active compound(s) is or are comprise in inert diluent(s) commonly used in the art (purified water, ethanol etc.).

Besides inert diluents, such compositions may also comprise adjuvants (wetting agents, suspending agents etc.), sweetening agents, flavouring agents, perfuming agents and preserving agents.

Other compositions for oral administration include spray compositions which may be prepared by known methods and which comprise one or more of the active compound(s).

Spray compositions may comprise additional substances other than inert diluents: e.g. stabilizing agents (sodium sulfite etc.), isotonic buffer (sodium chloride, sodium citrate, citric acid etc.).

For preparation of such spray compositions, for example, the method described in the U.S. Pat. Nos. 2,868,691 or 3,095,355 may be used.

Injections for parenteral administration include sterile aqueous or non-aqueous solutions, suspensions and emulsions. In such compositions, one or more of active compound(s) is or are admixed at least one of inert aqueous diluent(s) (distilled water for injection, physiological salt solution etc.) or inert non-aqueous diluent(s) (propylene glycol, polyethylene glycol, olive oil, ethanol, POLYSOLBATE 80 (registered trade mark) etc.).

Injections may comprise additional other than inert diluents: e.g. preserving agents, wetting agents, emulsifying agents, dispersing agents, stabilizing agents (lactose etc.), assisting agents such as assisting agents for dissolving (glutamic acid, aspertic acid etc.).

They may be sterilized, for example, by filtration through a bacteria-retaining filter, by incorporation of sterilizing agents in the compositions or by irradiation. They also be manufactured in the form of sterile solid compositions, for example, by freeze-drying, and which can be dissolved in sterile water or some other sterile diluents for injection immediately before used.

Other compositions for parenteral administration include liquids for external use, and endermic liniments (ointment etc.), suppositories and pessaries which comprise one or more of the active compound(s) and may be prepared by known methods.

Compositions for dermal administration, especially for the treatment and prevention of alopecia and acne, include liquids for external use such as lotion, tonic, spray, solution, suspension, emulsion and liniments such as ointment, gel, cream.

Such compositions may comprise one or more of active ingredient(s) and at least one of inert diluent(s), for example, distilled water, lower alcohols such as ethanol, higher alcohols such as cetanol, poly alcohols such as polyethylene glycol, propylene glycol, celluloses such as hydroxypropyl cellulose, animal or plant fats, vaseline, wax, silicone, plant oil such as olive oil, surfactants, zinc oxide etc.

Besides inert diluents, such composition may also comprise adjuvants (wetting agents, suspending agents, perfuming agents, preserving agents.

REFERENCE EXAMPLES AND EXAMPLES

The following reference examples and examples illustrate the present invention, but not limit the present invention.

Unless otherwise specified, "IR" were measured by KBr tablet method and "NMR" were measured in a solution of CDCl$_3$.

REFERENCE EXAMPLE 1

Synthesis of 4-(4-isobutylbenzyloxy)-2,3-dimethylbenzaldehyde

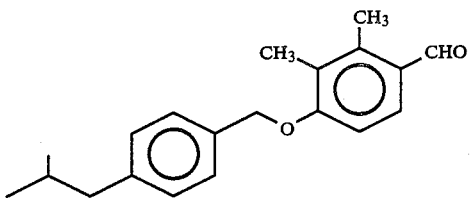

A mixture of 4-hydroxy-2,3-dimethylbenzaldehyde (220 mg), 4-isobutylbenzyl bromide (341 mg), potassium carbonate (1.38 g) and ethyl methyl ketone (10 ml) was refluxed for 6 hrs. After cooling, the reaction mixture was diluted with ethyl acetate, the solution was washed with dil hydrochloric acid, water, successively, dried and evaporated. The residue was purified by column chromatography on silica gel (hexane:EtOAc=10:1) to give the title compound (383 mg) having the following physical data:

TLC: Rf 0.48 (hexane:EtOAc=5:1); NMR: δ7.64 (1H, d), 7.32 (1H,d), 7.16 (1H,d), 5.12 (2H,s), 2.60 (3H,s), 2.48 (2H,d), 2.24 (3H,s), 1.94–1.80 (1H,m), 0.90 (6H,d).

REFERENCE EXAMPLE 2

Synthesis of 4-(4-isobutylbenzyloxy)-2,3-dimethylbenzoic acid

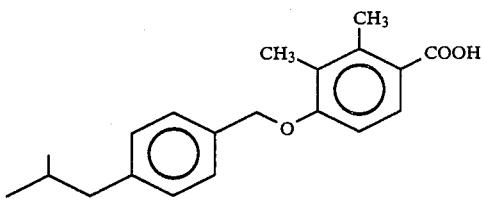

A solution of the aldehyde prepared in reference example 1 (380 mg) in acetone (5 ml) was cooled with ice. To the solution, Jones' reagent (2.67N; 2 ml) was dropped and allowed to stand. The solution was stirred for 1.5 hrs at room temperature. The reaction was stopped by adding of isopropyl alcohol. The crystals deposited were washed with hexane, dried and purified by column chromatography on silica gel (hexane-EtOAc) to give the title compound (328 mg) having the following physical data:

TLC: Rf 0.36 (hexane:EtOAc=2:1); NMR: δ7.80 (1H,d), 7.33 (1H, d), 7.15 (1H,d), 6.90 (1H,d), 5.09 (2H,s), 2.58 (3H,s), 2.48 (2H,d), 2.26 (3H,s), 0.91 (6H,d).

EXAMPLE 1

Synthesis of 4-[2-[4-(4-isobutylbenzyloxy)-2,3-dimethylbenzoylamino]phenoxy]butanoic acid ethyl ester

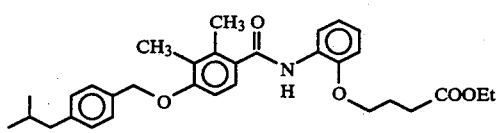

Oxyalyl chloride (2 ml) was dropped to a solution of the carboxylic acid prepared in reference example 2 (325 mg) in methylene chloride (2 ml). The solution was stirred for 1 hr and evaporated. To an ice-cooled mixture of ethyl 4-(2-aminophenoxy)butanoate (232 mg), pyridine (1 ml) and methylene chloride (15 ml), the above solution was dropped. The mixture was stirred for 30 mins at the same temperature and for 1 hr at room temperature. The reaction solution was washed with water, dried and evaporated. The residue was purified by column chromatography on silica gel (hexane:EtOAc=5:1) to give the title compound (383 mg) having the following physical data:

TLC: Rf 0.5 (hexane:EtOAc=3:1); NMR: 6 8.58–8.48 (1H,m), 8.05 (1H,s), 7.34 (H,d), 7.16 (1H,d), 7.08–6.96 (2H,m), 6.90–6.80 (2H,m), 5.07 (2H,s), 4.14–3.96 (4H,m), 2.49 (2H,d), 2.44 (3H,s), 1.18 (3H,t), 0.91 (6H,d).

EXAMPLE 2

Synthesis of 4-[2-[4-(4 isobutylbenzyloxy)-2 3-dimethylbenzoylamino]phenoxy]butanoic acid

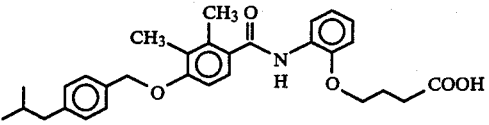

1N aq. Solution of lithium hydroxide (3 ml) was added to a solution of the ester Prepared in example 1 (380 mg) in dimethoxyethane (8 ml). The mixture was stirred for 30 mins at 50° C. After reaction, the solution was neutralized with dil. hydrochloric acid and was extracted with ethyl acetate. The extract was dried and evaporated. The residue obtained was recrystalized from hexane to give the title compound (317 mg) having the following physical data:

TLC: Rf 0.26 (hexane:EtOAc=1:1); mp: 143° C.

EXAMPLE 2(a)–2(dd)

By the similar procedure as reference example 1, 2 and example 1 and 2, compounds having the following physical data shown in the Table II. III and IV were given.

TABLE II

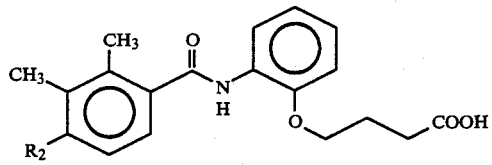

| No. | $R^2$— | Name | TLC (Rf) | mp or MS |
|---|---|---|---|---|
| 2 (a) | (benzyloxy) | 4-[2-(4-benzyloxy-2,3-dimethylbenzoyl amino)phenoxy]butanoic acid | 0.44 (CH$_2$Cl$_2$:EtOAc = 7:3) | 165–167° C. |
| 2 (b) | (2-methylbenzyloxy) | 4-[2-[4-(2-methylbenzyloxy)-2,3-dimethylbenzoylamino]phenoxy]butanoic acid | 0.16 (hexane:EtOAc = 2:1) | 125–127° C. |
| 2 (c) | (3-methylbenzyloxy) | 4-[2-[4-(3-methylbenzyloxy)-2,3-dimethylbenzoylamino]phenoxy]butanoic acid | 0.16 (hexane:EtOAc = 2:1) | 119–122° C. |
| 2 (d) | (4-methylbenzyloxy) | 4-[2-[4-(4-methylbenzyloxy)-2,3-dimethylbenzoylamino]phenoxy]butanoic acid | 0.15 (hexane:EtOAc = 2:1) | 142–145° C. |
| 2 (e) | (2,6-dimethylbenzyloxy) | 4-[2-[4-(2,6-dimethylbenzyloxy)-2,3-dimethylbenzoylamino]phenoxy]butanoic acid | 0.20 (hexane:EtOAc = 2:1) | 127–131° C. |

TABLE II-continued

| No. | R²— | Name | TLC (Rf) | mp or MS |
|---|---|---|---|---|
| 2 (f) | 4-ethylbenzyl-CH₂O— | 4-[2-[4-(4-ethybenzyloxy)-2,3-dimethylbenzoylamino]phenoxy]butanoic acid | 0.13 (hexane:EtOAc = 2:1) | 155–158° C. |
| 2 (g) | 4-propylbenzyl-CH₂O— | 4-[2-[4-(4-propylbenzyloxy)-2,3-dimethylbenzoylamino]phenoxy]butanoic acid | 0.14 (hexane:EtOAc = 2:1) | 137–141° C. |
| 2 (h) | 4-isopropylbenzyl-CH₂O— | 4-[2-[4-(4-isopropylbenzyloxy)-2,3-dimethylbenzoylamino]phenoxy]butanoic acid | 0.13 (hexane:EtOAc = 2:1) | 137–141° C. |
| 2 (i) | 4-chlorobenzyl-CH₂O— | 4-[2-[4-(4-chlorobenzyloxy)-2,3-dimethylbenzoylamino]phenoxy]butanoic acid | 0.47 (CH₂Cl₂:EtOAc = 2:1) | 156–160° C. |
| 2 (j) | 4-(cyclobutylmethyl)benzyl-CH₂O— | 4-[2-[4-(4-cyclobutylmethyl benzyloxy)-2,3-dimethylbenzoylamino]phenoxy]butanoic acid | 0.17 (hexane:EtOAc = 2:1) | 146–147° C. |
| 2 (k) | PhCH₂CH₂O— | 4-[2-[4-(2-phenylethoxy)-2,3-dimethylbenzoylamino]phenoxy]butanoic acid | 0.37 (CHCl₃:CH₃OH = 95:5) | 141–142° C. |
| 2 (l) | Ph(CH₂)₃O— | 4-[2-[4-(3-phenylpropoxy)-2,3-dimethylbenzoylamino]phenoxy[butanoic acid | 0.35 (CHCl₃:CH₃OH = 95:5) | 152° C. |
| 2 (m) | Ph(CH₂)₄O— | 4-[2-[4-(4-phenylbutoxy)-2,3-dimethylbenzoylamino]phenoxy]butanoic acid | 0.37 (CHCl₃:CH₃OH = 95:5) | 113° C. |
| 2 (n) | Ph(CH₂)₅O— | 4-[2-[4-(5-phenylpentyloxy)-2,3-dimethylbenzoylamino]phenoxy]butanoic acid | 0.11 (hexane:EtOAc = 2:1) | MS m/z 295, 189 |
| 2 (o) | 4-isobutylphenyl-CH(CH₃)O— | 4-[2-[4-[1-(4-isobutylphenyl)ethoxy]-2,3-dimethylbenzoylamino]phenoxy] butanoic acid | 0.37 (hexane:EtOAc = 1:1) | MS m/z 503, 345 |

TABLE II-continued

| No. | R²— | Name | TLC (Rf) | mp or MS |
|---|---|---|---|---|
| 2 (p) | [4-bis(4-propylphenyl)methoxy group] | 4-[2-[4-[bis(4-propylphenyl)methoxy]-2,3-dimethylbenzoylamino]phenoxy]butanoic acid | 0.32 (hexane:EtOAc = 1:1) | MS m/z 593, 551, 523 |
| 2 (q) | [diphenylmethoxy group] | 4-[2-(4-diphenylmethoxy)-2,3-dimethylbenzoylamino]phenoxy]butanoic acid | 0.37 (hexane:EtOAc = 1:1) | MS m/z 509, 361, 343, 315 |
| 2 (r) | [bis(4-propylphenyl)methylamino group] | 4-[2-[4-[bis(4-propylphenyl)methyl amino]-2,3-dimethylbenzoylamino] phenoxy]butanoic acid | 0.20 (hexane:EtOAc = 1:1) | MS m/z 592, 506, 398, 342, 251 |
| 2 (s) | [N,N-bis(4-propylphenylmethyl)amino group] | 4-[2-[4-[N,N-bis(4-propylphenyl methyl)amino]2,3-dimethylbenzoyl amino]phenoxy]butanoic acid | Rf 0.37 (hexane:EtOAc = 1:1) | MS m/z 606, 520, 473, 413, 278, 133 |
| 2 (t) | [N,N-bis(4-trifluoromethylphenylmethyl)amino group] | 4-[2-[4-[N,N-bis(4-trifluoromethyl phenylmethyl)amino]-2,3-dimethyl benzoylamino]phenoxy]butanoic acid | Rf 0.28 (hexane:EtOAc = 1:1) | MS m/z 658, 455, 304, 277 159, 132 |

TABLE II-continued

[Structure: 2,3-dimethyl-4-R2-benzoyl amide of 2-aminophenoxy butanoic acid]

| No. | R²— | Name | TLC (Rf) | mp or MS |
|---|---|---|---|---|
| 2 (u) | [4-CF₃-phenyl-CH₂-NH-] | 4-[2-[4-[N-(4-trifluoromethyl phenylmethyl)amino]-2,3-dimethylbenzoylamino]phenoxy]butanoic acid | Rf 0.20 (EtOAc) | MS m/z 500, 307, 277, 263, 183, 167, 159, 118 |
| 2 (v) | [bis(4-propylphenyl)methylthio-] | 4-[2-[4-[bis(4-propylphenyl)methylthio]-2,3-dimethylbenzoyl amino]phenoxy]butanoic acid | Rf 0.28 (EtOAc) | MS m/z 609, 359, 313, 252, 222, 193, 167 |
| 2 (w) | [N-methyl-5,6,7,8-tetrahydronaphth-1-yl-aminomethyl] | 4-[2-[4-[N-Methyl-N-(5,6,7,8-tetrahydronaphth-1-yl)aminomethyl]-benzoylamino]phenoxy]butanoic acid | Rf 0.30 (EtOAc) | MS m/z 500, 340, 312, 306, 161 |

TABLE III

[Structure: 4-(4-isobutylbenzyloxy)-R¹-substituted benzoyl amide of 2-amino-phenyl-A-butanoic acid]

| No. | R¹ (ring) | Name | TLC (Rf) | mp |
|---|---|---|---|---|
| 2 (x) | 2,3-dichlorophenyl, A = O | 4-[2-[4-(4-isobutylbenzyloxy)-2,3-dichlorobenzoylamino]phenoxy]butanoic acid | 0.47 (hexane:EtOAc = 1:3) | 139–140° C. |
| 2 (y) | indane-4,7-diyl, A = O | 4-[2-(7-(4-isobutylbenzyloxy)indane-4-carbonylamino]phenoxy]butanoic acid | 0.27 (hexane:EtOAc = 1:1) | 156–157° C. |

TABLE III-continued

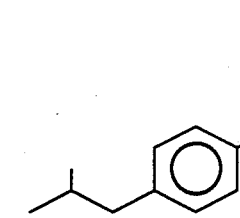

| No. | R¹ / structure | Name | TLC (Rf) | mp |
|---|---|---|---|---|
| 2 (z) | H, A=O (tetrahydronaphthalene) | 4-[2-[4-(4-isobutylbenzyloxy)-5,6,7,8-tetrahydronaphthalene-1-carbonylamino]phenoxy]butanoic acid | 0.50 (hexane:EtOAc = 1:1) | 164° C. |
| 2 (aa) | naphthalene, A=O | 4-[2-[4-[4-isobutylbenzyloxy)naphthalene-1-carbonylamino]phenoxy]butanoic acid | 0.27 (hexane:EtOAc = 1:1) | 156–157° C. |
| 2 (bb) | H, A=S (tetrahydronaphthalene) | 4-[2-[4-(4-isobutylbenzyloxy)-5,6,7,8-tetrahydronaphthalene-1-carbonylamino]phenylthio]butanoic acid | 0.39 (hexane:EtOAc = 1:1) | 135° C. |

TABLE IV

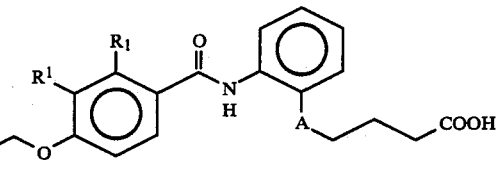

| No. | R²— | Name | TLC (Rf) | MS |
|---|---|---|---|---|
| 2 (cc) | 4-propylbenzyloxy | 4-[2-[4-(4-propylbenzyloxy)-2,3-dimethylbenzoylamino)phenylthio]butanoic acid | 0.40 (hexane:EtOAc = 2:1) | m/z 491, 372, 434, 281 |
| 2 (dd) | 1-(4-isobutylphenyl)ethoxy | 4-[2-[4-[1-(4-isobutylphenyl)ethoxy]-2,3-dimethylbenzoylamino]phenylthio]butanoic acid | 0.31 (hexane:EtOAc = 2:1) | m/z 519, 359, 309 |

EXAMPLE 3

Synthesis of 4-[2-[4-(4-propylbenzyloxy)-2,3-dimethylbenzoylamino]phenylsulfinyl]butanoic acid

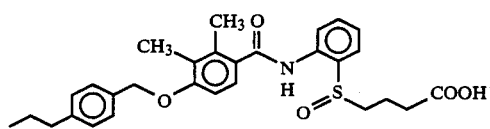

A solution of sodium periodate (3.85 g) in water (84 ml) was added to a solution of the compound prepared in example 2(cc) (6.3 g) in methanol (340 ml). The mixture was stirred for 12 hrs at room temperature. To the mixture, a solution of sodium periodate (1.28 g) in water (30 ml) was added and the mixture was stirred for 3 hrs at room temperature. The reaction solution was filtered, and the filtrate was concentrated to dryness. Toluene was added to the residue, the mixture was distilled azeotropically. The residue was purified by column chromatography on silica gel (chloroform-methanol), and further recrystalization from a mixture of benzene and hexane to give the title compound (6.39 g) having the following physical data:

TLC: Rf 0.53 (chloroform:methanol=9:1); IR: $\nu$ 3600–2300, 1760, 1650, 1585, 1460, 1270, 1100, 1000, 760 cm$^{-1}$.

EXAMPLE 4

(−)-4-[2-(4-[1-(4-isobutylphenyl)ethoxy]-2,3-dimethyl benzoylamino phenoxy]butanoic acid The compounds prepared in example 2(o) (403 mg) and cinchonidine (2.36 g) were dissolved into acetone (70 ml) with heating. The solution was allowed to stand to give white crystals. The crystals were gathered by filtration, and purified by recrystalization from acetone four times. The white crystals obtained were dissolved into chloroform. The solution was washed with dil. hydrochloric acid. The oily layer was washed with water, dried and evaporated to give the title compound having the following physical data:
Appearance: white crystal;
Optical angle of rotation: $[\alpha]_D$ −39.6° (c=1, CHCl$_3$).

EXAMPLE 5

Sodium salt of (−)-4-[2-[4-[1-(4-isobutylphenyl)ethoxy]-2,3-dimethyl benzoylamino)phenoxy]butanoic acid The compound prepared in example 4 was dissolved into methanol. The equivalent molar of an aq. Sodium hydroxide solution was added and evaporated to give the title compound having the following data:

IR: $\nu$ 3050, 1750, 1580, 1560, 1510, 1445, 1260, 1090, 1020, 740 cm$^{-1}$.

Formulation example

The following components were admixed in conventional method and punched out to obtain 100 tablets each containing 50 mg of active ingredient.

| | |
|---|---|
| 4-[2-[4-(4-isobutylbenzyloxy)-2,3-dimethylbenzoylamino]phenoxy]butanoic acid | 5 g |
| Cellulose calcium gluconate (disintegrating agent) | 0.2 g |
| Magnesium stearate (lubricating agent) | 0.1 g |
| Microcrystaline cellulose | 4.7 g |

What is claimed is:
1. A benzoylaminophenoxybutanoic acid derivative of formula:

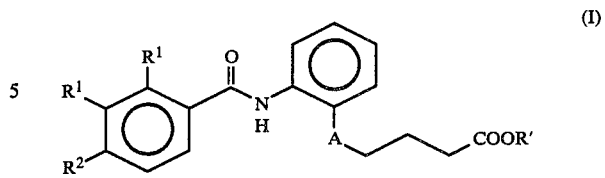

(I)

wherein R' is hydrogen or alkyl of from 1 to 4 carbon atom(s); A is oxygen atom, sulfur atom or sulfinyl (SO) group; both R$^1$'s are methyl or chlorine, or the two R$^1$'s and the carbon atoms of the benzine ring to which the two R$^1$'s are linked together are cyclopentane, cyclohexane or a benzene ring; and R$^2$ represents a group of formula:

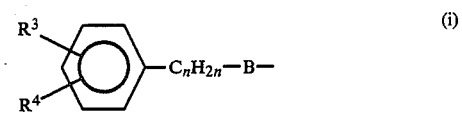

(i)

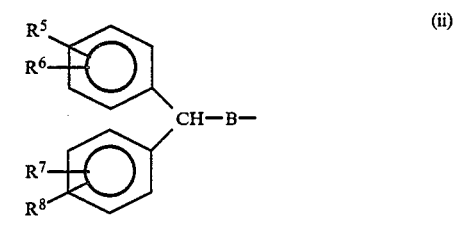

(ii)

or (iii)

wherein B is oxygen, sulfur or a group of formula: NR$^{11}$ wherein R$^{11}$ is hydrogen or alkyl of from 1 to 4 carbon atom(s), R$^3$, R$^4$, R$^5$, R$^6$, R$^7$ and R$^8$ are, independently, hydrogen alkyl of from 1 to 4 carbon atoms(s), halogen, trifluoromethyl or cyclobutylmethyl, m is 0 or 1, n is an integer of from 1 to 5, and R$^9$ is a hydrogen, alkyl of from 1 to 5 carbon atom(s) or a group of formula:

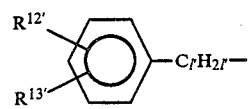

or

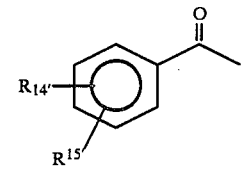

wherein $R^{12}$, $R^{13}$, $R^{14}$ and $R^{15}$ are, independently, hydrogen, alkyl of from 1 to 4 carbon atom(s), halogen, trifluoromethyl or cyclobutylmethyl, and l is an integer of from 1 to 4, and
$R^{10}$ is a group of the formula:

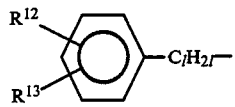

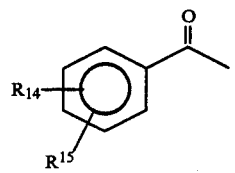

or

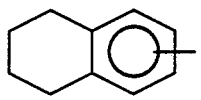

wherein $R^{12}$, $R^{13}$, $R^{14}$, and $R^{15}$, are, independently, hydrogen, alkyl of from 1 to 4 carbon atom(s), halogen, trifluoromethyl or cyclobutylmethyl, and l' is an integer of from 1 to 4; or non-toxic salts thereof.

2. A compound according to claim 1, wherein $R^2$ is a group of formula (i).

3. A compound according to claim 2, wherein the two $R^2$'s both are methyl.

4. A compound according to claim 1, wherein $R^2$ is a group of the formula (ii).

5. A compound according to claim 1, wherein $R^2$ is a group of formula (iii).

6. A compound according to claim 1 or 3, which is:
4-(2-(4-benzyloxy-2,3-dimethylbenzoylamino)-phenoxy)butanoic acid,
4-(2-(4-(2-methylbenzyloxy)-2,3-dimethylbenzoylamino)phenoxy) butanoic acid,
4-(2-(4-(3-methylbenzyloxy)-2,3-dimethylbenzoylamino)phenoxy) butanoic acid,
4-(2-(4-(4-methylbenzoyloxy)-2,3-dimethylbenzoylamino)phenoxy) butanoic acid,
4-(2-(4-(2,6-dimethylbenzoyloxy)-2,3-dimethylbenzoylamino) phenoxy) butanoic acid,
4-(2-(4-(4-ethylbenzyloxy)-2,3-dimethylbenzoylamino)phenoxy) butanoic acid,
4-(2-(4-(4-propylbenzyloxy)-2,3-dimethylbenzoylamino)phenoxy) butanoic acid,
4-(2-(4-(4-isopropylbenzyloxy)-2,3-dimethylbenzoylamino) phenoxy) butanoic acid,
4-(2-(4-(4-isobutylbenzyloxy)-2,3-dimethylbenzoylamino)phenoxy) butanoic acid,
4-(2-(4-(4-chlorobenzyloxy)-2,3-dimethylbenzoylamino)phenoxy) butanoic acid,
4-(2-(4-(4-cyclobutylmethylbenzyloxy)-2,3-dimethylbenzoylamino) phenoxy) butanoic acid, 4-(2-(4-(2-phenylethoxy)-2,3-dimethylbenzoylamino)-phenoxy) butanoic acid,
4-(2-(4-(3-phenylpropoxy)-2,3-dimethylbenzoylamino)phenoxy) butanoic acid,
4-(2-(4-(4-phenylbutoxy)-2,3-dimethylbenzoylamino)phenoxy) butanoic acid,
4-(2-(4-(5-phenylpentyloxy)-2,3-dimethylbenzoylamino)phenoxy) butanoic acid,
4-(2-(4-(4-isobutylphenyl)ethoxy)-2,3-dimethylbenzoylamino) phenoxy) butanoic acid,
4-(2-(4-(4-propylbenzyloxy)-2,3-dimethylbenzoylamino)phenylthio) butanoic acid,
4-(2-(4-(1-(4-isobutylphenyl)ethoxy)-2,3-dimethylbenzoylamino) phenylthio) butanoic acid,
4-(2-(4-(4-propylbenzyloxy)-2,3-dimethylbenzoylamino)phenylsulfinyl) butanoic acid or
4-(2-(4-(N-(4-trifluoromethylphenylmethyl)amino)-2,3-dimethylbenzoylamino)phenoxy) butanoic acid.

7. A compound according to claim 2, wherein the two $R^1$'s both are chlorine, or the two $R^1$'s and the carbon atoms of the benzene ring to which the two $R^1$'s are linked together are cyclopentane, cyclohexane or a benzene ring.

8. A compound according to claim 1, which is:
4-(2-(4-(4-isobutylbenzyloxy)2,3-dichlorobenzoylamino)phenoxy) butanoic acid,
4-(2-(7-(4-isobutylbenzyloxy)indane-4-carbonylamino)phenoxy) butanoic acid,
4-(2-(8-(4-isobutylbenzyloxy)-5,6,7,8-tetrahydronaphthalene-1-carbonylamino)phenoxy) butanoic acid,
4-(2 (4-(4-isobutylbenzloxy)naphthalene-1-carbonylamino)phenoxy) butanoic acid or
4-(2-(8-(4-isobutylbenzyloxy)5,6,7,8-tetrahydronaphthalene-1-carbonylamino)phenylthio) butanoic acid.

9. A compound according to claim 1 or 4, which is:
4-(2-(4-(bis(4-propylphenyl)methoxy)-2,3-dimethylbenzoylamino)phenoxy) butanoic acid,
4-(2-(4-diphenylmethoxy)-2,3-dimethylbanzoylamino)phenoxy) butanoic acid,
4-(2-(4-(bis(4-propylphenyl)methylamino)-2,3-dimethylbenzoylamino)phenoxy) butanoic acid or
4-(2-(4-(bis(4-propylphenyl)methylthio)-2,3-dimethylbenzoylamino)phenoxy) butanoic acid.

10. A compound according to claim 1 or 5, which is:
4-(2-(4-(N,N-bis(4-propylphenylmethyl)amino)-2,3-dimethylbenzoylamino)phenoxy) butanoic acid
4-(2-(4-(N,N bis(4-trifluoromethylphenylmethyl)amino)-2,3-dimethylbenzoylamino)phenoxy) butanoic acid or
4-(2-(4-(N-methyl-N-(5,6,7,8-tetrahydronaphth-1-yl)aminomethyl)-2,3-dimethylbenzoylamino)-phenoxy) butanoic acid 11. A pharmaceutical composition for treating alopecia, acne or prostatic hypertrophy which comprises as active ingredient, an effective amount of benzoylaminophenoxybutanoic acid derivative of formula (I) depicted in claim 1 and a pharmaceutically acceptable carrier and/or coating.

* * * * *

UNITED STATES PATENT AND TRADEMARK OFFICE
CERTIFICATE OF CORRECTION

PATENT NO. : 4,980,372
DATED : DECEMBER 25, 1990
INVENTOR(S) : HISAO NAKAI ET AL

It is certified that error appears in the above-identified patent and that said Letters Patent is hereby corrected as shown below:

Claim 1, column 28, lines 55-60, in the structural formula, change " $R^{15}$ " to -- $R^{15'}$ --;

column 29, line 1, change " $R^{12}$, $R^{13}$, $R^{14}$ and $R^{15}$ " to -- $R^{12'}$, $R^{13'}$, $R^{14'}$ and $R^{15'}$ --;

column 29, line 4, change " 1 " to -- 1' --;

column 29, line 29, (fourth line after the last structural formula), change " 1' " to -- 1 --.

Claim 3, column 29, line 34, change " $R^{2}$'s " to -- $R^{1}$'s --.

Claim 6, column 30, line 9, change " 4-(2-(4-(4-isobutylphenyl) " to -- 4-(2-(4-(1-(4-isobutylphenyl) --.

UNITED STATES PATENT AND TRADEMARK OFFICE
CERTIFICATE OF CORRECTION

PATENT NO. : 4,980,372

DATED : DECEMBER 25, 1990

INVENTOR(S) : HISAO NAKAI ET AL

It is certified that error appears in the above-identified patent and that said Letters Patent is hereby corrected as shown below:

Claim 8, column 30, line 25, after " claim 1 " insert -- or 7 --;

column 30, line 33, change " 4-(2 (4-(4-isobutylbenzloxy) " to -- 4-(2-(4-(4-isobutylbenzloxy) --.

UNITED STATES PATENT AND TRADEMARK OFFICE
CERTIFICATE OF CORRECTION

PATENT NO. : 4,980,372
DATED : DECEMBER 25, 1990
INVENTOR(S) : HISAO NAKAI ET AL

It is certified that error appears in the above-identified patent and that said Letters Patent is hereby corrected as shown below:

Claim 9, column 30, line 41, change

" 2,3-dimethylban "    to

-- 2,3-dimethylben --;

column 30, line 50, change

" 4-(2-(4-N,N bis "    to

-- 4-(2-(4-N,N-bis --.

Signed and Sealed this

Thirtieth Day of March, 1993

Attest:

STEPHEN G. KUNIN

Attesting Officer

Acting Commissioner of Patents and Trademarks